United States Patent
Shirai et al.

(10) Patent No.: US 8,029,820 B2
(45) Date of Patent: Oct. 4, 2011

(54) PATCHES CONTAINING TULOBUTEROL

(75) Inventors: Sadanobu Shirai, Takamatsu (JP);
Masahiro Yamaji, Higashikagawa (JP);
Osamu Yoshimoto, Takamatsu (JP);
Mamoru Naruse, Itano-gun (JP);
Kenichi Hattori, Tokushima (JP);
Takako Sueda, Aki-gun (JP)

(73) Assignee: Teikoku Seiyaku Co., Ltd., Kagawa-Ken (JP)

( * ) Notice: Subject to any disclaimer, the term of this patent is extended or adjusted under 35 U.S.C. 154(b) by 0 days.

(21) Appl. No.: 10/524,858

(22) PCT Filed: Jun. 16, 2004

(86) PCT No.: PCT/JP2004/008777
§ 371 (c)(1), (2), (4) Date: Feb. 18, 2005

(87) PCT Pub. No.: WO2004/112770
PCT Pub. Date: Dec. 29, 2004

(65) Prior Publication Data
US 2005/0220852 A1    Oct. 6, 2005

(30) Foreign Application Priority Data

Jun. 20, 2003  (JP) ................ 2003-176799

(51) Int. Cl.
*A61F 13/02* (2006.01)
(52) U.S. Cl. ...................... 424/448; 424/449
(58) Field of Classification Search ......... None
See application file for complete search history.

(56) References Cited

U.S. PATENT DOCUMENTS

| 5,254,348 A |   | 10/1993 | Hoffmann et al. |
| 5,312,627 A | * | 5/1994 | Stroppolo et al. ............ 424/448 |
| 5,639,472 A |   | 6/1997 | Yamamoto et al. |
| 5,866,157 A | * | 2/1999 | Higo et al. .................... 424/448 |
| 6,117,447 A |   | 9/2000 | Nakano et al. |
| 7,056,528 B1 | * | 6/2006 | Bracht ........................ 424/449 |

FOREIGN PATENT DOCUMENTS

| AU | 199668374 | 5/1997 |
| EP | 0 788 792 | 8/1997 |
| EP | 1 074 251 | 2/2001 |
| JP | 63-10716 | 1/1988 |
| JP | 5-194202 | 8/1993 |
| JP | 7-285854 | 10/1995 |
| JP | 11-228395 | 8/1999 |
| WO | 97/14411 | 4/1997 |
| WO | 01/28531 | 4/2001 |

OTHER PUBLICATIONS

B. D. Kim et al., "The penetration enhancement of β2-selective agonist, tulobuterol, across the hairless mouse skin", Proceedings—28th International Symposium on Controlled Release of Bioactive Materials and 4th Consumer & Diversified Products Conference, vol. 1, pp. 167 to 168, 2001.

* cited by examiner

*Primary Examiner* — Robert A Wax
*Assistant Examiner* — Hasan Ahmed
(74) *Attorney, Agent, or Firm* — Wenderoth, Lind & Ponack, L.L.P.

(57) ABSTRACT

A patch containing tulobuterol in the low concentration and having the stable release-controllability, prepared by laminating an adhesive layer consisting of a rubber, an adhesive resin and a plasticizer on a backing, wherein 1 to 4 w/w % of tulobuterol in the lower concentration as an active ingredient and 0.1 to 3 w/w % of a higher fatty acid as a drug-releasing controlling agent are contained in the adhesive layer.

4 Claims, 4 Drawing Sheets

PATCHES CONTAINING TULOBUTEROL

TECHNICAL FIELD

The present invention relates to a dermally absorbable type patch containing tulobuterol.

BACKGROUND ART

Various dermally absorbable type preparations containing tulobuterol have been recently proposed as preparations making up the demerits of the oral preparation containing tulobuterol (See Japanese Patent Publication A 11-228395, Japanese Patent No. 2753800 (Japanese Patent Publication A 7-285854), WO 97/14411 and Japanese Patent No. 2633089 (Japanese Patent Publication A 5-194202)).

A patch prepared by dissolving tulobuterol into an adhesive has such a demerit as the duration necessary to sustain its effective serum concentration is not attained.

Therefore, techniques to increase the concentration of tulobuterol or to contain much amount of it by thickening an adhesive layer have been tried.

For example, in Japanese Patent Publication A 11-228395, a tulobuterol-patch which has a structure to fully dissolve tulobuterol is proposed. However, when such a patch is preserved for a long time due to the high concentration of tulobuterol, the preparation is apt to receive the influence by changes of circumstances such as temperature, etc. For example, even if the preparation has a good quality just after preparing it, with the passage of time there is a possibility that drug-release pattern becomes different from one at the earlier time because tulobuterol crystallizes in the adhesive layer or changes of the concentration occurs.

In general essential physical properties such as adhesivity and shape retention of a patch are broken down and it is impossible to stably release the drug when a large amount of ingredients, which are either essential or unessential, are contained in the patch.

In regard to a patch containing much amount of tulobuterol, when the amount of an adhesive is too much, the essential physical properties become worse and during application of the patch, it gives an uncomfortable feeling to a patient and there is also a possibility to drop it out due to rubbing with clothes.

Further, in regard to a patch in which tulobuterol is much dissolved in the higher concentration, it can not help containing much amount of tulobuterol and therefore, it is neither economical nor practical.

On the other hand, a patch in which both soluble type tulobuterol and crystalline type tulobuterol are contained in the specific rates (see Japanese Patent No. 2753800), a patch prepared by recrystallizing tulobuterol in an adhesive (see WO97/14411), a patch consisting of tulobuterol and a specific co-polymer, wherein tulobuterol is suspended or microcapsulized and they are included in the adhesive layer, or a patch prepared by constructing matrix layers, adhesive layers or reservoir layers, and by laminating theses layers (see Japanese Patent No. 2633089), etc., were proposed as a dermally absorbable type patch which is aimed for a long lasting preparation of tulobuterol.

However, in regard to these patches, when they are preserved for long time, they are apt to receive the influence by changes of circumstances such as temperature, etc. For example, owing to the temperature rising in summer, tulobuterol in crystals, suspensions or microcapsules contained in the patch dissolves and on the contrary, owing to the temperature dropping in winter, the dissolved tulobuterol begins to crystallize. Also in case of laminated type preparations, owing to changes of circumstances, movement (transfer) of ingredients such as tulobuterol and other ingredients occurs between matrix laminated layers and reservoir-layers, and the release pattern of tulobuterol from the patch is changed and there is a possibility to give the influence to the therapeutic effect of tulobuterol.

As well, these patches require complex techniques for suspending tulobuterol, microcupsulation of it and stable blending it into the matrix, and selection of the condition for recrystallization of it in the matrix, construction of the matrix and the reservoir layer, laminating, etc. They are problematic.

DISCLOSURE OF INVENTION

The object of the present invention is to provide a patch in which tulobuterol is contained in the lower concentration, but the patch has controllability of stable drug-release.

The present inventors have been extensively studied in consideration of the above problems and as a result, have found that a patch prepared by containing tulobuterol in the lower concentration in an adhesive layer which was prepared by suitably combining a higher fatty acid, a rubber, an adhesive resin and a plasticizer, shows unexpectedly the drug-release in therapeutically effective amount and an ability to easily control drug-releasing pattern, is hardly influenced by changes of the passage with time and furthermore, has essential physical properties such as adhesivity and shape pretension which are adjustable, and the process for preparation thereof is simple. Thus the present invention has been completed.

BEST MODE FOR CARRYING OUT THE INVENTION

Figure 1:
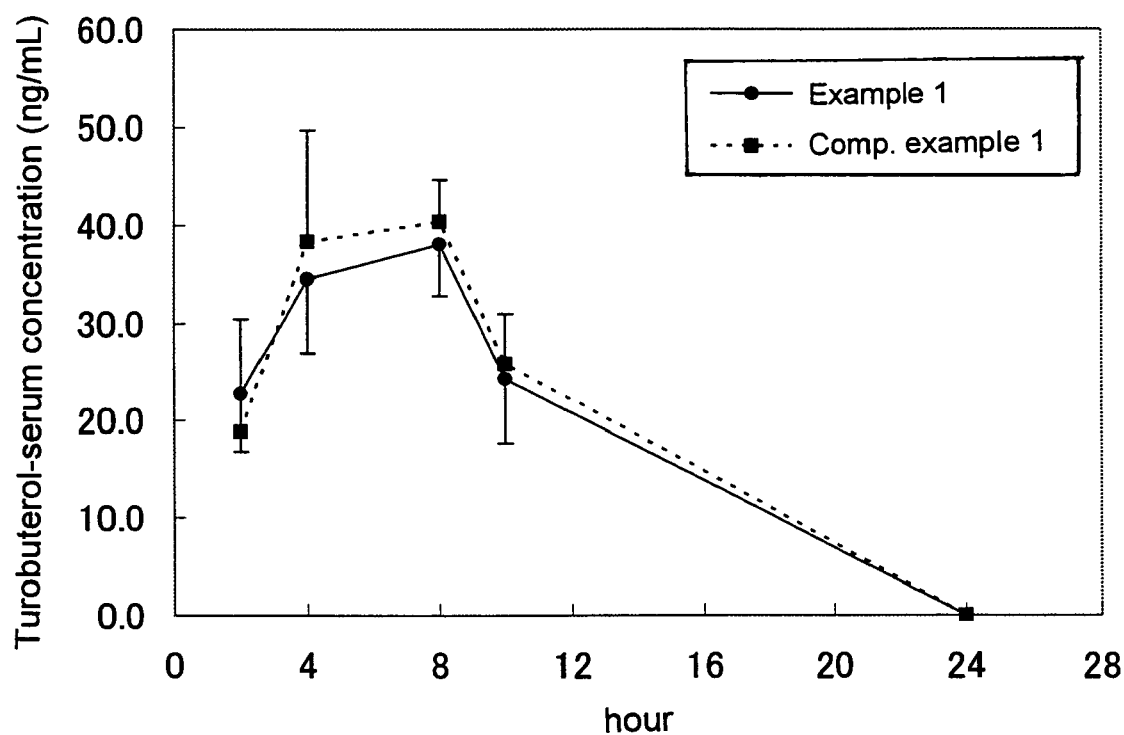
FIG. 1 shows changes of a passage with time of tulobuterol-serum concentration in case of applying patches of Example 1 and Comparative example 1.

Namely, the present invention relates to a patch containing tulobuterol prepared by laminating an adhesive layer consisting of a rubber, an adhesive resin and a plasticizer on a backing, wherein 1 to 4 w/w % of tulobuterol as an active ingredient and 0.1 to 3 w/w % of a higher fatty acid, preferably C11-22 fatty acid, especially preferably C14-18 fatty acid as a drug-release controlling agent are contained in the said adhesive layer.

The present invention also relates to a patch containing tulobuterol, wherein 5 to 35 w/w % of the rubber, 20 to 70 w/w % of the adhesive resin to 60 w/w % of the plasticizer are contained in the above adhesive layer.

In regard to patches containing tulobuterol which have been traditionally proposed, it has been considered that it is essential to blend an acrylic adhesive which has a large polar or reactive group, or an adhesive resin having a large polarity such as a rosin in an adhesive layer.

However the patch related to the present invention does not need such substances, and that it is found that to blend such substances in an adhesive layer is not rather preferable because such substances cause to give great influences to release pattern of tulobuterol and stability in changes of the passage with time.

The constitution of the patch preparation of the present invention is illustratively explained below.

Tulobuterol which is contained as an active ingredient in the preparation of the present invention is dermally absorbed and exhibits an effect as a bronchodilator, and the preparation is characterized in containing tulobuterol in its small amount of 1~4 w/w %. When the amount is less than 1%, the area of application must be broadened in order to make the therapeutic effects exhibit. When the amount is beyond 4 w/w %, it is necessary to admix other ingredients to control the drug-release because the concentration of the drug becomes high and the drug is contained much. And as a result, there is a possibility to break down essential physical properties as a patch. These amounts therefore, are not preferable.

The higher fatty acid admixed in the present preparation has an activity to stably control release pattern of tulobuterol, and is used for the drug-release controlling agent. The higher fatty acid includes $C_{11-22}$) preferably $C_{14-18}$ fatty acid, such as linolic acid, linolenic acid, oleic acid, stearic acid, palmitic acid, lauric acid, myristic acid, isostearic acid, ricinolic acid, etc., especially preferably oleic acid and stearic acid.

The amount is 0.1~3 w/w %, preferably 0.2~2 w/w %, more preferably 0.3~1 w/w %. When the amount is less than 0.1 w/w %, tulobuterol is quickly released, and when the amount is beyond 3 w/w %, the drug-release is excessively controlled. Therefore these amounts are not preferable.

The rubber admixed in the present preparation has an ability to control the strength of an adhesive. The rubber includes a natural rubber, a synthetic rubber, such as isoprene rubber, styrene-butadiene rubber, styrene.butadiene block copolymer, styrene.isoprene block copolymer, preferably a synthetic rubber from the viewpoint of quality, especially preferably styrene.isoprene block copolymer.

The amount is usually 5-35 w/w %, preferably 10-30 w/w %, especially preferably 15-25 w/w %. When the amount is less than 5 w/w %, the strength of the adhesive does not become enough, and when the amount is beyond 35 w/w %, the strength becomes too high and the sticking power decreases.

The adhesive agent admixed in the present preparation has an ability to control the adhesive strength of an adhesive. The adhesive agent includes petroleum resin, polyterpene resin, polyolefin resin, saturated alicyclic hydrocarbon resin, etc., especially preferably petroleum resin, and saturated alicyclic hydrocarbon resin.

The amount is usually 20-70 w/w %, preferably 30-60 w/w %, especially preferably 40-55 w/w %. When the amount is less than 20%, the adhesivity of the adhesive agent does not become enough, and when the amount is beyond 70 w/w %, the sticking power becomes too high. Therefore, these amounts are not preferable.

The plasticizer admixed in the present preparation has an ability to control the viscosity of the adhesive and is used to delicately control essential physical properties, such as sticking power, strength and improvement of sensibility. The plasticizer includes a liquid resin, an oil, liquid paraffin, polybutene, etc., especially preferably liquid paraffin and polybutene.

The amount is usually 5-60 w/w %, in accordance with the amounts of a rubber and an adhesive agent contained.

The preparation of the present invention is prepared by wrapping the adhesive layer having the above mentioned constituents with both a backing and a release liner. The weight of the adhesive layer is 20~200 g/m², preferably 50~150 g/m². When the weight is less than 20 g/m², the sticking power becomes very weak and when the weight is beyond 200 g/m², the sticking power becomes excessively strong and therefore, there is a possibility to injure the applied skin. Furthermore, to increase the weight without any object is not preferable from the economical viewpoint.

The backing is not limited as long as it is usually used and thereon an adhesive can be extended. However, a preferable backing is one that does not give excessively undesirable feeling to the skin during application and fully keep the adhesive in order not to remain on the skin when releasing off. Also the preferable backing is one which does not absorb tulobuterol, such a polyester film as polyethyleneterephthalate (PET), a polypropylene film, and paper, a fabric, or an unwoven fabric laminated on thereon.

The liner is preferable one which does not absorb tulobuterol, such a polyester film as polyethyleneterephthalate (PET) etc., or its laminated film. The liner is preferable easily releasable from an adhesive when it is released. If necessary, a release agent such as silicon resin may be spread on the adhesive surface of the liner.

The suitable method for preparing the present preparation is a dry method. For example, constituents of an adhesive are dissolved in an organic solvent and the resulting solution is uniformly spread out on the one side of the liner. The treated liner is dried to remove the solvent and is stuck on the backing. Thus prepared patch is cut in a suitable size to be packed in a sealed package.

A hot-melt method as another method is considered. Namely the constitutions of an adhesive are blended and melted at about 100-200° C. and then, spread on the liner at the same temperature. The preparation is cooled to prepare a patch.

This method has a merit in the viewpoint not to use an organic solvent, but the constituents are denatured to some extent as the heat charge is very large. Therefore, essential physical properties and the release pattern of tulobuterol, etc., become unstable and the high processing technique is necessary for preparing it. Therefore, this method can not be chosen as the first option from the practical viewpoint.

EXAMPLE

The present invention is explained by illustrating examples and test-examples, but the present invention is not limited by these examples.

Example 1

| Adhesive | Content (w/w %) |
| --- | --- |
| Tulobuterol | 2 |
| Oleic acid | 0.5 |
| Styrene · isoprene · styrene block copolymer | 20 |
| Saturated alicyclic hydrocarbon (Petroleum resin) | 48 |
| Polybutene | 10 |
| Liquid paraffin | 19 |

| Adhesive | Content (w/w %) |
|---|---|
| Dibutylhydroxytoluene | 0.5 |
| Weight of adhesive | 100 g/m² |
| Backing | PET 10 μm |
| Liner | PET 75 μm |
| | (Release coating on one side) |

According to the above indications, tulobuterol and oleic acid were dissolved in a suitable amount of toluene (Solution A). On the other hand, styrene·isoprene·styrene block copolymer, saturated alicyclic hydrocarbon resin, polybutene, liquid paraffin and dibutylhydroxytoluene were mixed with a suitable amount of toluene until being homogenous (Mixture B).

The solution A and the mixture B were stirred until being homogenous, and the mixture was spread on the release coated surface of the polyethyleneterephthalate (PET) liner in the amount of 100 g/m² and dried. The PET backing was laminated on the adhesive side of the liner and the product was cut in a suitable size to be packed in a sealed package.

Example 2

| Adhesive | Content (w/w %) |
|---|---|
| Tulobuterol | 2.5 |
| Oleic acid | 1 |
| Styrene·isoprene·styrene block copolymer | 25 |
| Saturated alicyclic hydrocarbon resin (Petroleum resin) | 43 |
| Polybutene | 8 |
| Liquid paraffin | 20 |
| Dibutylhydroxytoluene | 0.5 |
| Weight of adhesive | 125 g/m² |
| Backing | PET 3.5 μm/paper |
| Liner | PET 75 μm |
| | (Release coating on one side) |

According to the above indications and in the same manner as in the method of Example 1, a patch was prepared.

Example 3

| Adhesive | Content (w/w %) |
|---|---|
| Tulobuterol | 2 |
| Stearic acid | 0.7 |
| Styrene·isoprene·styrene block copolymer | 18 |
| Saturated alicyclic hydrocarbon resin (Petroleum resin) | 50 |
| Polybutene | 5 |
| Liquid paraffin | 23.8 |
| Dibutylhydroxytoluene | 0.5 |
| Weight of adhesive | 90 g/m² |
| Backing | PET 3.5 μm/Unwoven fabric |
| Liner | PET 75 μm |
| | (Release coating on one side) |

According to the above indications and in the same manner as in the method of Example 1, a patch was prepared.

Example 4

| Adhesive | Content (w/w %) |
|---|---|
| Tulobuterol | 3 |
| Oleic acid | 0.5 |
| Styrene·isoprene·styrene block copolymer | 20 |
| Saturated alicyclic hydrocarbon resin (Petroleum resin) | 42 |
| Polybutene | 10 |
| Liquid paraffin | 23.5 |
| Dibutylhydroxytoluene | 1.0 |
| Weight of adhesive | 80 g/m² |
| Backing | PET 12 μm |
| Liner | PET 75 μm |
| | (Release coating on one side) |

According to the above indications and in the same manner as in the method of Example 1, a patch was prepared.

Comparative Example 1

The commercially available crystalline type tulobuterol patch (Trade name: Hokunalin tape prepared by Hokuriku Seiyaku K.K.): Tulobuterol: 10 w/w %, 2 mg/sheet, size of sheet: 10 cm²

Comparative Example 2

By using the same ingredients as in Example 2 provided that in place of the oleic acid 1 w/w %, liquid paraffin 1 w/w % was used, a patch was prepared in the same manner as in the method of Example 1.

Comparative Example 3

By using the same ingredients as in Example 2 provided that in place of saturated alicyclic hydrocarbon 43 w/w %, rosin glycerin ester 43 w/w % was used, a patch was prepared in the same manner as in the method of Example 1.

Comparative Example 4

| Adhesive | Content (w/w %) |
|---|---|
| Tulobuterol | 5.5 |
| Styrene·isoprene·styrene block copolymer | 56.8 |
| Diolefin·olefin copolymer | 37.7 |
| Weight of adhesive | 250 g/m² |
| Backing | PET 25 μm |
| Liner | PET 75 μm |
| | (Release coating on one side) |

According to the above indications, styrene·isoprene·styrene block copolymer and diolefin·olefin block copolymer were stirred at 150° C. Thereto was added tulobuterol and the stirred mixture was passed through between release treated PET liner and PET backing during being kept at 110° C. and it was rolled under the constant pressure in order to become 250 g/m² in thickness. The obtained patch was cut in a suitable size to be packed in a sealed package.

This preparation is a highly concentrated, highly contained and soluble type tulobuterol patch prepared by the method of example (sample 2a) of Japanese Patent No. 2633089.

Comparative Example 5

| Adhesive | Adhesive layer 5-1 Content (w/w %) | Adhesive layer 5-2 Content (w/w %) |
|---|---|---|
| Tulobuterol | 1 | 5.5 |
| Styrene · isoprene · styrene block copolymer | 61.3 | 56.8 |
| Diolefin · olefin copolymer | 37.7 | 37.7 |
| Weight of adhesive | 50 g/m$^2$ | 200 g/m$^2$ |
| Backing | PET 25 μm (Release coating on one side) | PET 25 μm (Release coating on one side) |
| Liner | PET 75 μm (Release coating on one side) | PET 75 μm (Release coating on one side) |

According to the above indications, an adhesive layer 5-1 and an adhesive layer 5-2 were prepared in the same manner as in Comparative example 4. After removing each PET backing, each adhesive surface was stuck each other to prepare a laminated tulobuterol patch preparation. The preparation was cut in a suitable size to be packed in a sealed package. This preparation is a laminated and soluble type tulobuterol patch prepared by the method of Japanese Patent No. 2633089.

Comparative Example 6

| Adhesive | Content (w/w %) |
|---|---|
| Tulobuterol | 5 |
| Isopropyl myristate | 40 |
| Styrene · isoprene · styrene block copolymer | 38.5 |
| Polyisobutylene | 5.5 |
| Saturated alicyclic hydrocarbon resin (Petroleum resin) | 11 |
| Weight of adhesive | 40 g/m$^2$ |
| Backing | PET 25 μm |
| Liner | PET 75 μm (Release coating on one side) |

According to the above indications, styrene.isoprene.styrene block copolymer, polyisobutylene and saturated alicyclic hydrocarbon resin were mixed until being homogenous. To the mixture were added and mixed tulobuterol and isopropyl myristate until being homogenous. The solution was spread on the surface of release treated PET in the amount of 40 g/m$^2$ dried and stuck on PET backing. Thus obtained preparation was cut in a suitable size to be packed in a sealed package.

This preparation was a highly concentrated and soluble type tulobuterol patch prepared by example 8 of Japanese Patent Publication A 11-228395.

Test 1

A patch of Example 1 (tulobuterol: 2 w/w %, size: 10 cm$^2$) and a commercially available patch of Comparative example 1 were applied to the back of a hair-cut rat respectively. Two, four, eight, ten and twenty four hours later, the blood was taken and tulobuterol levels in serum were measured by HPLC. Changes of the passage with time of tulobuterol levels in serum on application of patches of Example 1 and Comparative example 1 were shown in FIG. 1.

From this test result, it was suggested that a patch of Example 1 maintained for a long time tulobuterol levels in serum as same as the commercialized patch of Comparative example 1, which contains 5 times amount of tulobuterol as much as the patch of Example 1 has. Therefore, it was shown that the patch of the present invention was a lower concentrated and soluble type patch, and had an ability to control the drug-release for a long time.

Furthermore, according to the disclosure of WO 97/14411, the crystalline type tulobuterol patch requires to adjust the average particle size of tulobuterol within 2~20 μm, in order to stabilize the drug-release from the patch and its duration. Therefore, due to crystallizing tulobuterol during adjusting the particle size in the adhesive layer, the ageing process for controlling time and temperature is required.

On the contrast, the patch of Example 1 is a lower concentrated and soluble type tulobuterol patch and has drug-release ability without containing its crystals. Therefore, it was cleared that the process for preparing for this patch did not require the above mentioned complex ageing processes and the patch could be prepared by a very simple procedure.

Test 2

The skin of abdomen of a hair-cut rat was extracted and fitted on a Frantz-diffusion cell. Phosphate-buffer was used as a reservoir solution and the cell was kept to stir at 37° C. during test.

A patch of Example 1, and patches of Comparative examples 2 and 3 were cut in a circle having diameter 13 mm (Tulobuterol of Example 1 and Comparative examples: 2 w/w %, 200 μg/cm$^2$), and the circles fitted on the extracted skin. Small amount of the reservoir solution was from time to time taken and the amount of permeated tulobuterol was measured by HPLC (Drug permeation test on rat-extracted skin).

Figure 2:
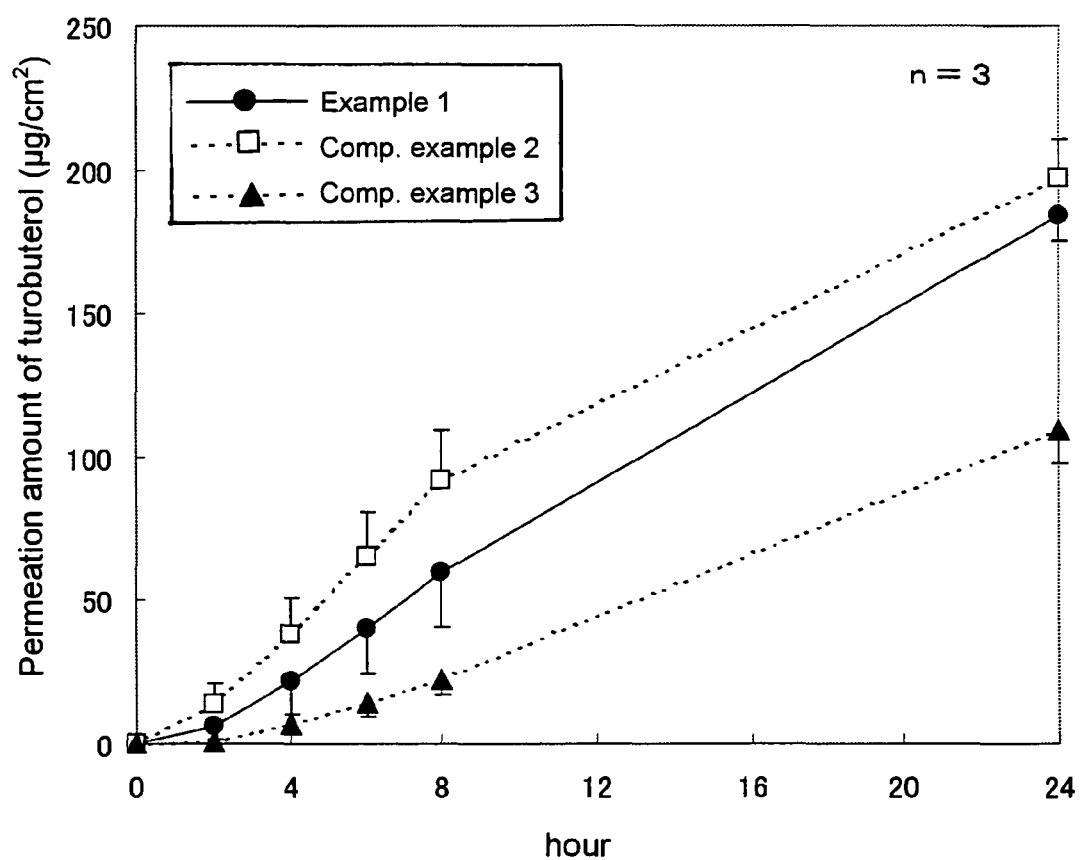
FIG. 2 shows changes of the passage with time of tulobuterol-permeability on extracted rat-skin in case of applying patches of Example 1, Comparative example 2 and Comparative example 3.

Changes of the passage with time of permeated tulobuterol in case of application of patches of Example 1 and Comparative examples 2 and 3 were shown in FIG. 2.

Example 1: tulobuterol; 2 w/w %, 200 μg/cm$^2$

Comparative example 2 and 3: tulobuterol; 2 w/w %, 200 μg/cm$^2$

From this test result, the amount of permeated tulobuterol in regard to the patch of Example 1 was constant in changes of the passage with time. On the other hand, in regard to the patch of Comparative example 2 without containing a higher fatty acid, it showed the tendency that the amount of the permeated drug increased and the duration decreased at a latter half. Furthermore, in Comparative example 3 containing rosin glycerin ester having polarity, the drug permeability greatly decreased.

Test 3

Influence on Drug-Release by Preservation Temperature

In order to check the influence on drug-release due to the changes of preservation temperature, patches of Example 1, Comparative examples 1, 4 and 6 were preserved in incubator kept at 4° C. and 40° C. respectively for 3 weeks, and then the temperature was adjusted to room temperature. In the same manner as Test 2 the drug permeation test on the skin extracted from rat was carried out.

Figure 3:
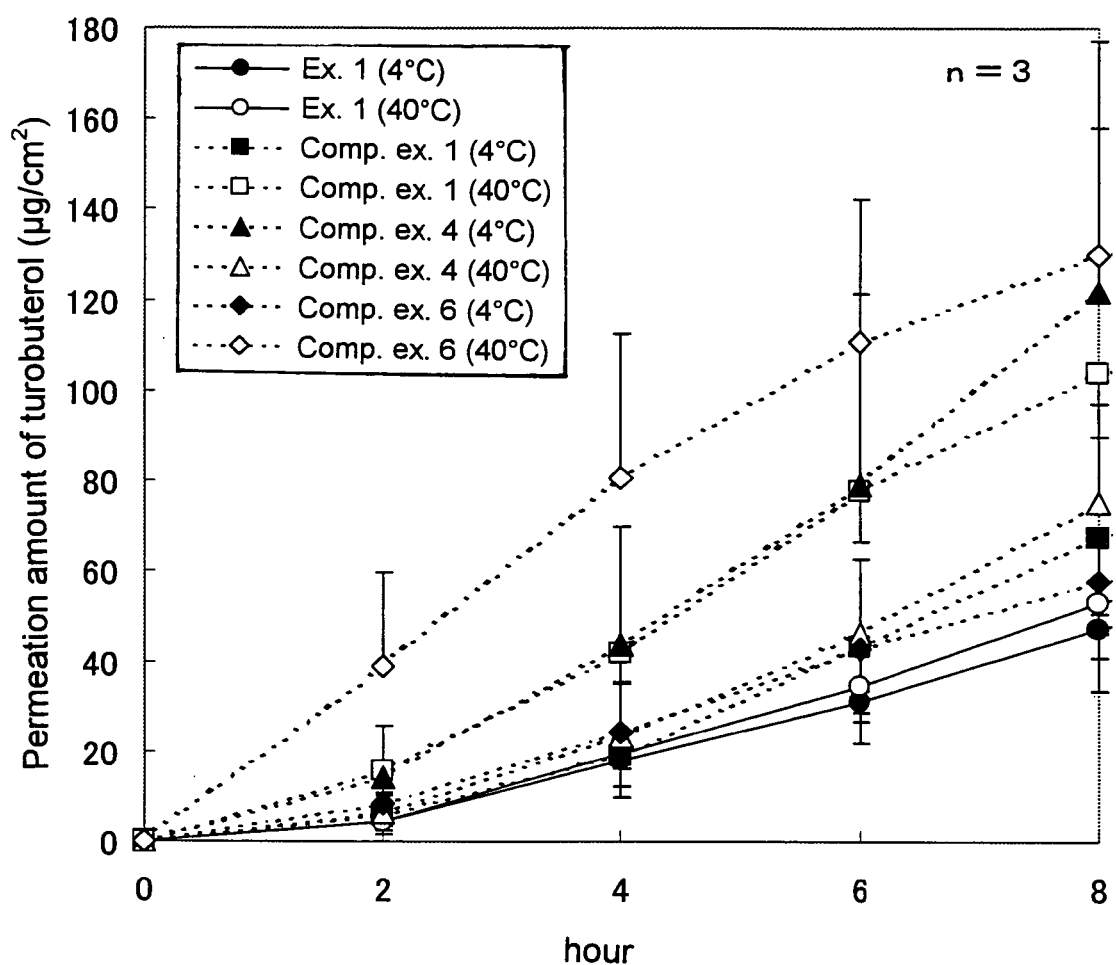
FIG. 3 shows changes of the passage with time of tulobuterol-permeability on extracted rat-skin in case of applying patches of Example 1, Comparative example 1, Comparative example 4 and Comparative example 6.

In case of application of patches of Example 1, Comparative examples 1, 4 and 6, changes of the passage with time of the permeation of tulobuterol were shown in FIG. 3. The drug-permeation rate due to changes of preservation temperature was shown in Table 1.

Example 1: tulobuterol; 2 w/w %, 200 μg/cm$^2$

Comparative example 1: tulobuterol; 10 w/w %, 200 μg/cm$^2$ (Crystalline Type Tulobuterol Patch)

Comparative example 4: tulobuterol; 5.5 w/w %, 1375 μg/cm² (Highly concentrated, highly contained and soluble type tulobuterol patch)

Comparative example 6: tulobuterol; 5 w/w %; 200 μg/cm² (Highly concentrated and soluble type tulobuterol patch)

TABLE 1

Rate of drug permeated amount due to changes of preservation temperature on each sample

| Test example | Example 1 | Comparative example 1 | Comparative example 4 | Comparative example 6 |
|---|---|---|---|---|
| Rate of permeation | 89%* | 65% | 162% | 44% |

*Example of calculation: {permeation amount of Example 1 (4° C.) (8 hr)}/{permeation amount of Example 1 (40° C.) (8 hr)} × 100

From this test result, it was shown that the drug permeated amount on a patch of Example 1 was constant and hardly influenced by changes of preservation temperature.

On the other hand, it was shown that the group of Comparative examples was apt to receive the influence by the changes of preservation temperature.

This fact suggested that due to changes of preservation temperature, the rate of crystals and dissolved portion in the adhesive was changed and due to the high concentration of the drug, the degree of saturation in the adhesive was changed, or since the drug was easy to separate from the constituents of the additive, it was possible that the amount of permeation of the drug was greatly changed up and down.

Test 4
Influence on Drug-Release by Preservation Term

In order to see the influence on drug-release by preservation term, by using two kinds of patches of Example 4, which was prepared 12 hours before and which was preserved for 2 months at room temperature, and two kinds of patches prepared by sticking layers 5-1 and 5-2 in Comparative example 5, which was prepared 12 hours before, and which was preserved for 2 months at room temperature, in the same manner as in Test 2, the drug permeation test on the skin extracted from rat was carried out. In regard to patches of Comparative example 5, the 5-1 layer side which was lower in the drug concentration was applied to the skin.

Figure 4:
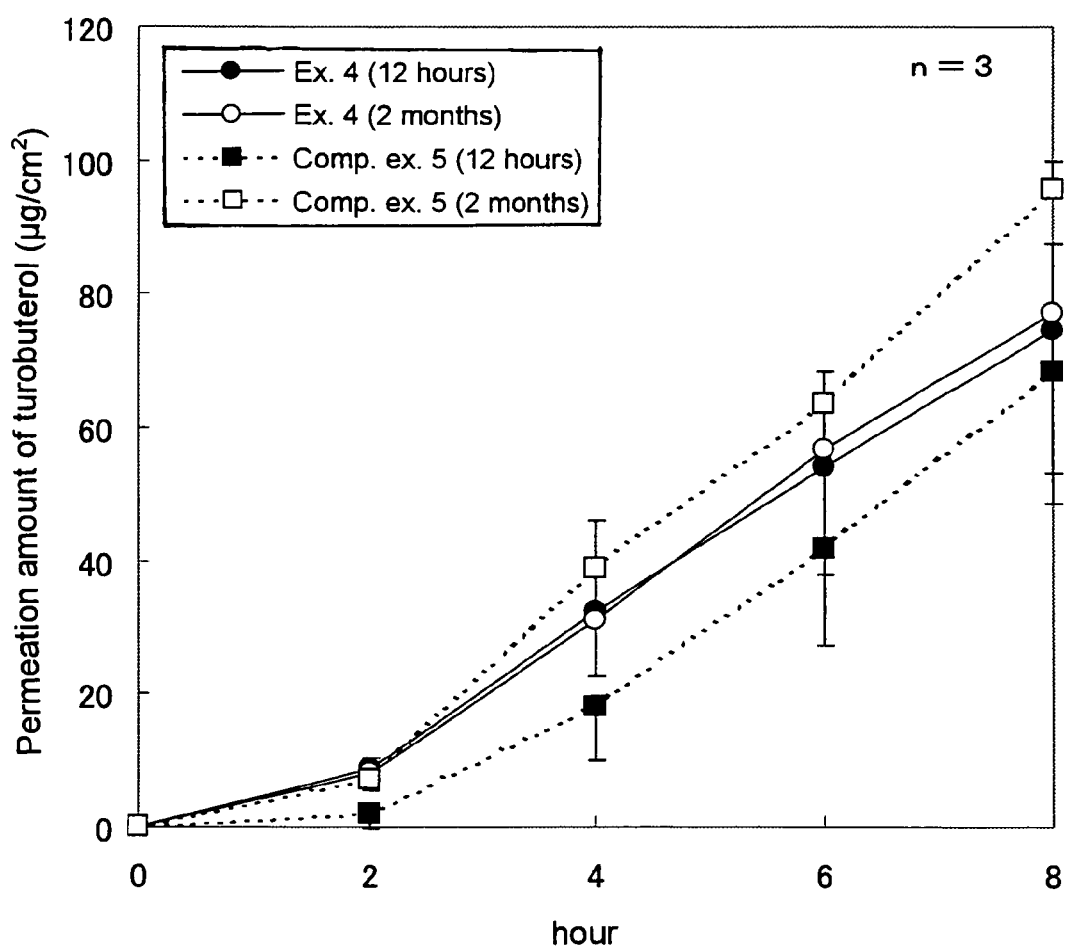
FIG. 4 shows changes of the passage with time of tulobuterol-permeability on extracted rat-skin in case of applying patches of Example 4 and Comparative example 5.

Changes of the passage with time of permeated tulobuterol in case of application of patches of Example 4 and Comparative example 5 were shown in FIG. 4.

Example 4: tulobuterol; 3 w/w %, 240 μg/cm²

Comparative example 5: (adhesive layer 5-1) tulobuterol; 1 w/w %, 50 μg/cm²+(adhesive layer 5-2) tulobuterol; 5.5 w/w %, 1108 μg/cm²

(Laminated Patch)

From this test result, it was shown that a patch of Example 4 was constant in drug permeation amount with changes of the passage with time.

On the other hand, in regard to a patch of Comparative example 5, the drug permeation amount was increased with changes of the passage with time. Even if the adhesive had the higher drug concentration, the drug permeation amount was controllable by sticking the layers having the lower drug concentration, but it was considered that the transfer between adhesive layers occurred and the concentration of the drug was averaged during a long time and therefore the control of the drug-release was injured.

INDUSTRIAL APPLICABILITY

The patch of the present invention is prepared by dissolving tulobuterol in the lower concentration in an adhesive layer and thereto adding a higher fatty acid, a rubber, an adhesive agent and a plasticizer in a suitable amount respectively, can easily control the tulobuterol release pattern and is excellent in changes of the passage with time of release pattern.

Furthermore, according to the present invention, essential physical properties on a patch such as adhesivity and shape retention are suitably adjusted and by simplifying the method for preparation, the patch of the present invention has following advantages comparing with the known tulobuterol-patch:

(1) Despite fact that the content of tulobuterol is less, the effect can be optimized according to the therapeutic object as the patch of the present invention shows sufficient tulobuterol release amount and it is possible to widely and simply control the tulobuterol release amount.

(2) The adjustment of essential properties as a patch is possible together with controlling the release amount and releasing pattern of tulobuterol. Therefore, it becomes possible to provide a patch which is therapeutically effective and has physical properties suitable to the skin condition.

(3) During preservation, the influence by changes of circumstances is less and the quality is stably kept for a long term.

(4) The preparation method is very simple and practical.

The invention claimed is:

1. A patch prepared by laminating an adhesive layer consisting of a rubber, an adhesive resin other than an acrylic adhesive, a plasticizer, 1 to 4 w/w % of tulobuterol as an active ingredient and 0.1 to 3 w/w % of a higher fatty acid as a drug-release controlling agent on a backing.

2. The patch according to claim 1 wherein 5 to 35 w/w % of the rubber, 20 to 70 w/w % of an adhesive resin and 5 to 60 w/w % of a plasticizer are contained in the adhesive layer.

3. The patch according to claim 1 wherein the higher fatty acid is $C_{11-22}$ fatty acid.

4. The patch according to claim 1 wherein the adhesive resin is selected from the group consisting of petroleum resin, polyterpene resin, polyolefin resin and saturated alicyclic hydrocarbon resin.

* * * * *